(12) United States Patent
Dryer

(10) Patent No.: US 8,575,112 B2
(45) Date of Patent: Nov. 5, 2013

(54) SMALL PEPTIDE MODULATORS OF POTASSIUM CHANNEL TRAFFICKING

(75) Inventor: Stuart E. Dryer, Houston, TX (US)

(73) Assignee: University of Houston System, Houston, TX (US)

( * ) Notice: Subject to any disclaimer, the term of this patent is extended or adjusted under 35 U.S.C. 154(b) by 400 days.

(21) Appl. No.: 12/807,900

(22) Filed: Sep. 16, 2010

(65) Prior Publication Data

US 2011/0086795 A1    Apr. 14, 2011

Related U.S. Application Data

(60) Provisional application No. 61/277,011, filed on Sep. 18, 2009.

(51) Int. Cl.
*A61K 38/08* (2006.01)

(52) U.S. Cl.
USPC ........ 514/21.8; 514/21.7; 514/17.4; 530/329; 530/330

(58) Field of Classification Search
None
See application file for complete search history.

(56) References Cited

U.S. PATENT DOCUMENTS 5,976,816 A * 11/1999 Alkon et al. .................. 435/7.21

OTHER PUBLICATIONS

Kim, 2007, Neuroscience, 146, 1552-1661.*
Gabashvili 2007, JARO, 8, 305-328.*
Carrigan, 2005, Analytical Biochemistry, 341, 290-298.*
Kim. Alternatively spliced C-terminal domains regulate the surface expression of large conductance calcium-activated potassium channels, Neuroscience, Jun. 8, 2007, abstract, vol. 146 (4), Elsevier.
Kim, Canonical Transient Receptor Potential Channel (TRPC) 3 and TRPC6 Associate with Large-Conductance Ca2+Activated K+(BKCa) Channels:Role in BKCa Trafficking to the Surface of Cultured Podocytes, Mol Pharmacol, Mar. 31, 2009, pp. 466-477, vol. 75(3), USA.
Chiu, Dominant-Negative Regulation of Cell Surface Expression by a Pentapeptide Motif at the Extreme COOH Terminus of an Slo1 Calcium Activated Potassium Channel Splice Variant, Mol Pharmacol, Jan. 5, 2010, pp. 497-507, vol. 77(4), USA.
Kim, Neph1 regulates steady-state surface expression of Slo1 Ca2+activated K+ channels: different effects in embryonic neurons and podocytes, Am J Phsiol Cell Physiol, 2009, pp. C1379-C1388, vol. 297.

* cited by examiner

*Primary Examiner* — Satyanarayana R Gudibande
(74) *Attorney, Agent, or Firm* — Benjamin Aaron Adler

(57) ABSTRACT

Provided herein are peptide modulators of ion channels. Specifically, the peptide modulators comprise the amino acid sequence VEDEC wherein V is valine, E is glutamate, D is aspartate, C is cysteine. In certain embodiments, the modulator is attached to the C-terminal end of Slo1 protein isoform. The present invention also claims conjugations of the first valine that make the peptide modulator more membrane permeable, such as myristoyl moieties and arginine-rich cell penetrating peptides. The present invention contemplates use of the peptide modulators in the treatment of diseases/malfunctions such as epilepsy, chronic pain, migraine, asthma, chronic obstructive pulmonary disease, urinary incontinence, hypertension, erectile dysfunction, irritable bowel syndrome, renal disorders of electrolyte imbalance, and possibly in certain kinds of cancer.

6 Claims, 9 Drawing Sheets

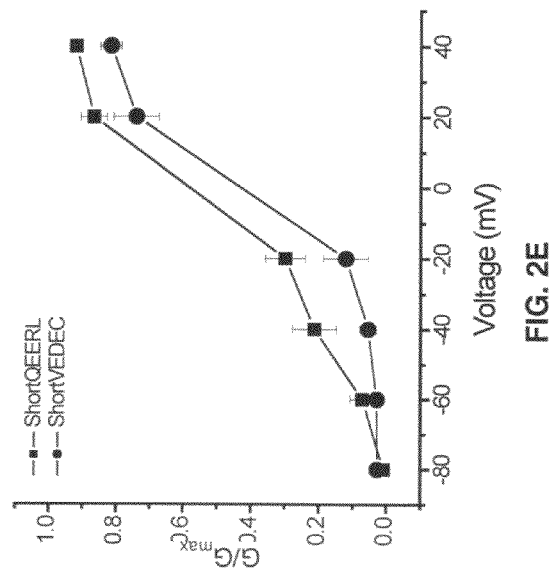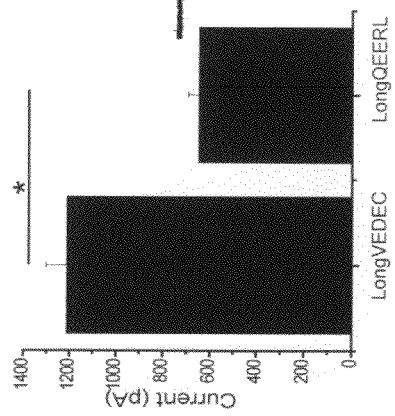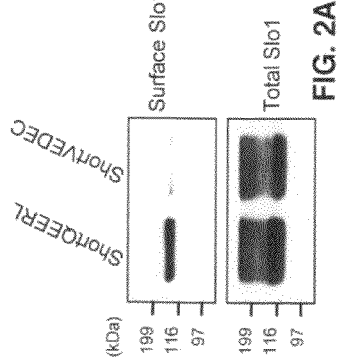

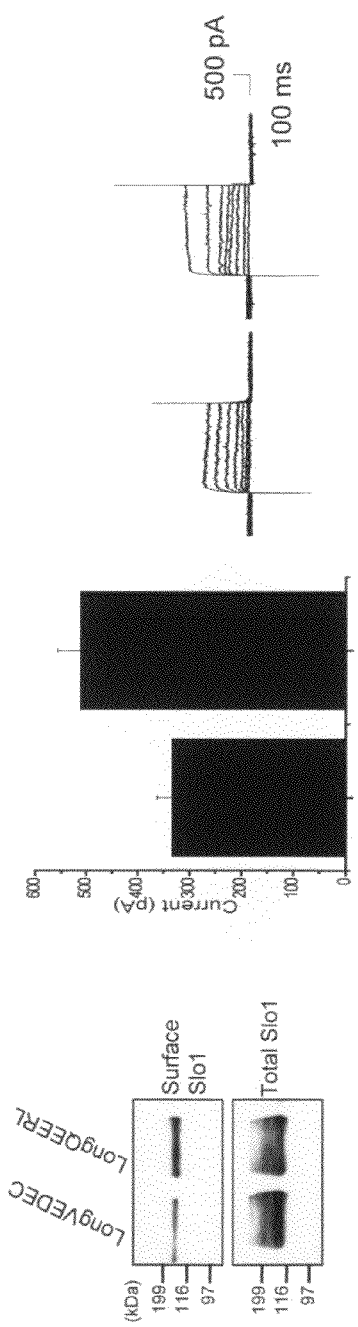
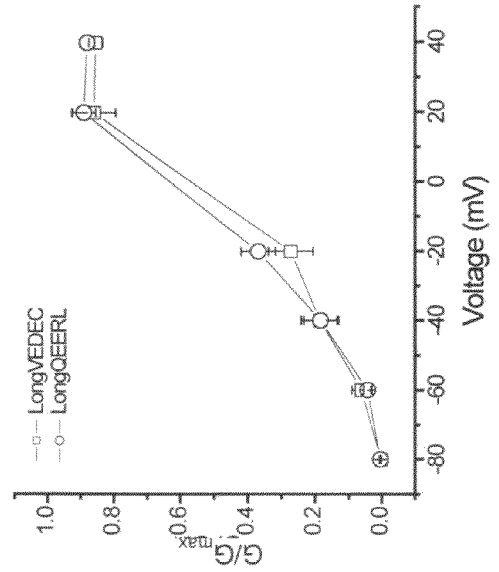
FIG. 3A
FIG. 3B
FIG. 3C
FIG. 3D
FIG. 3E

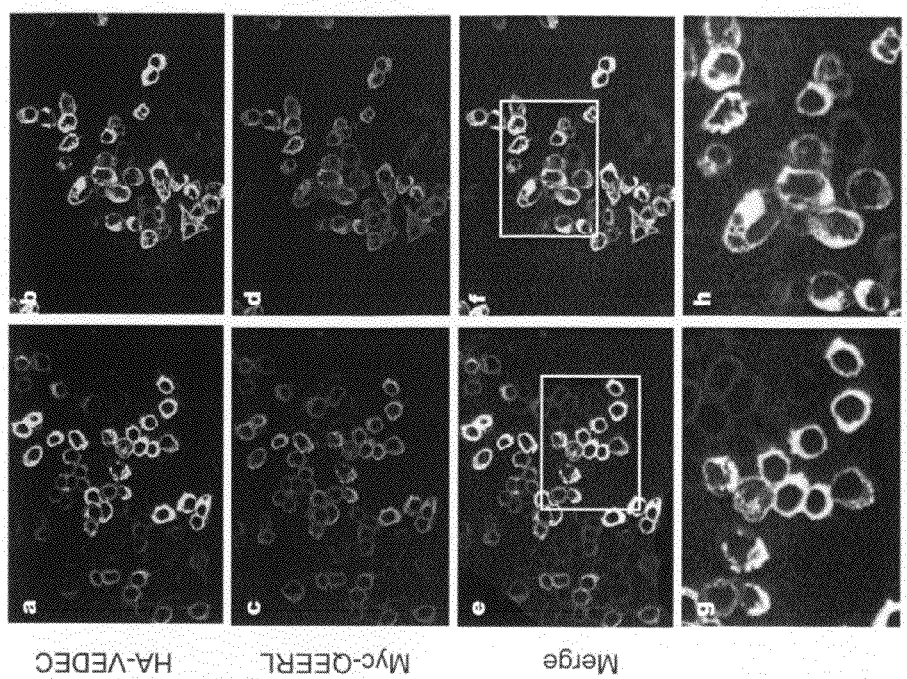
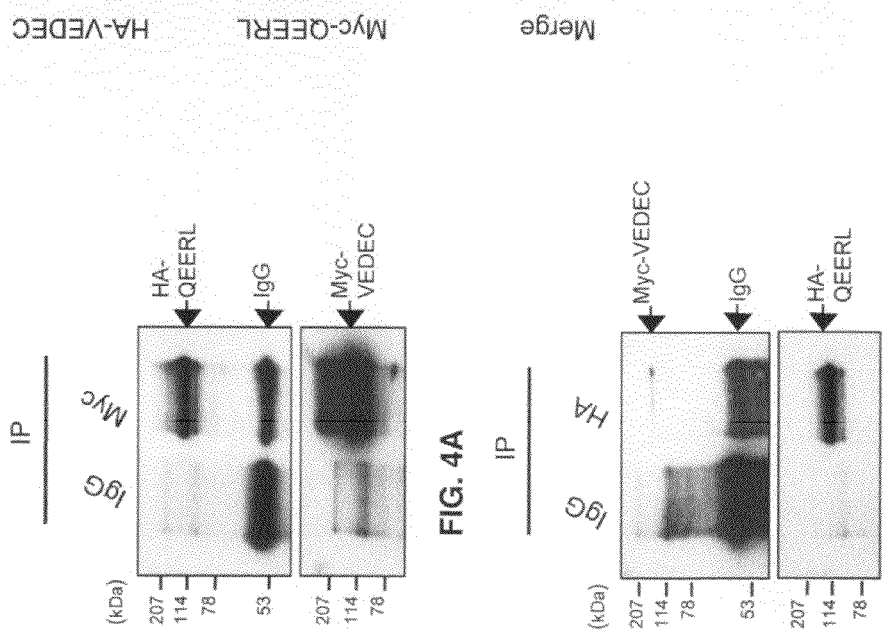

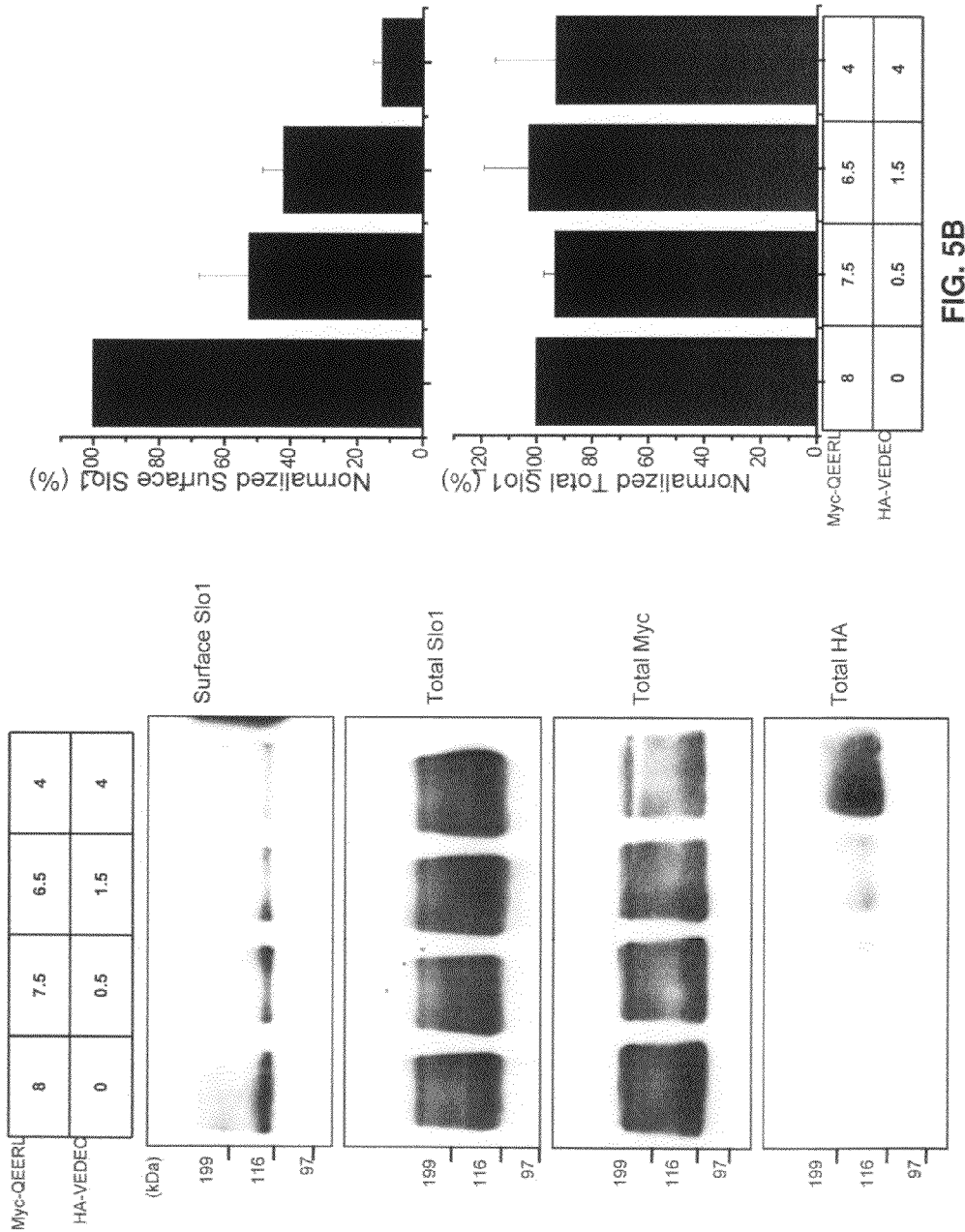

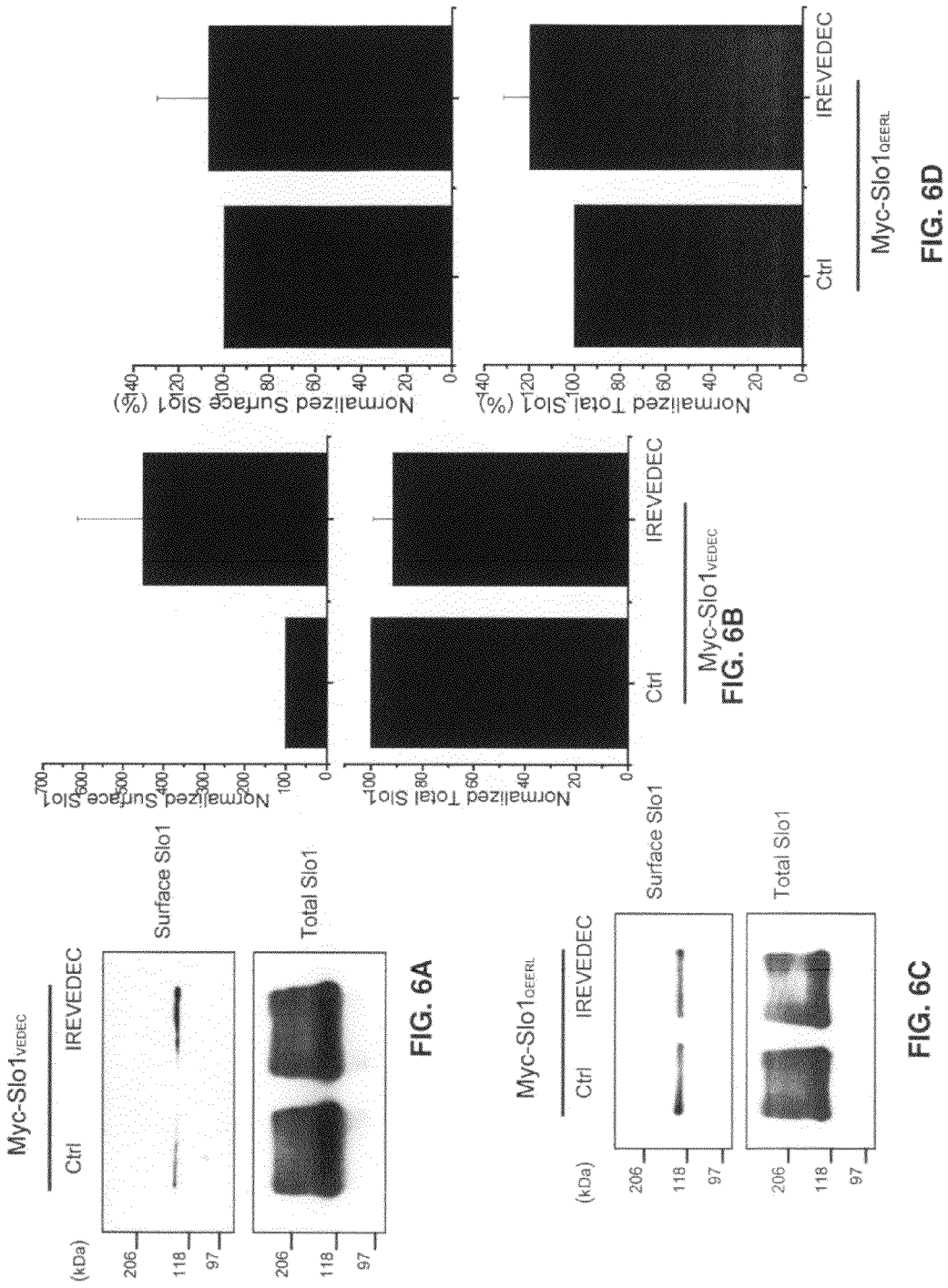

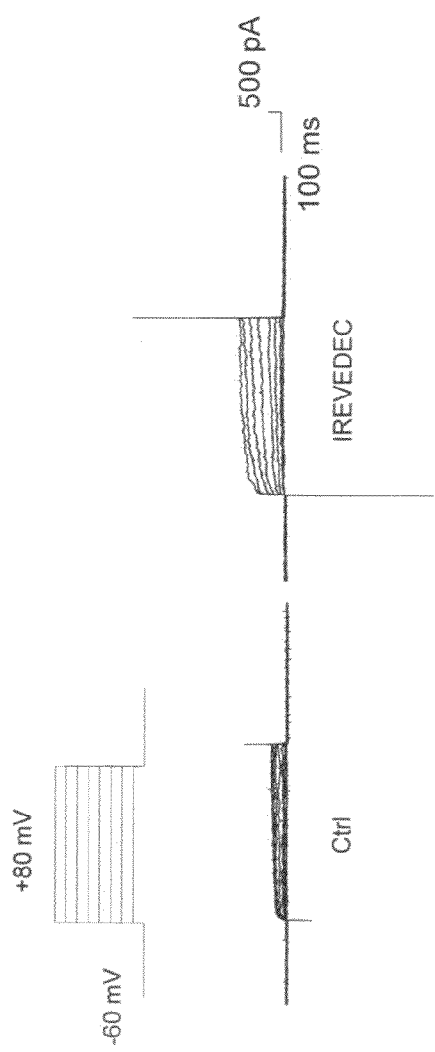
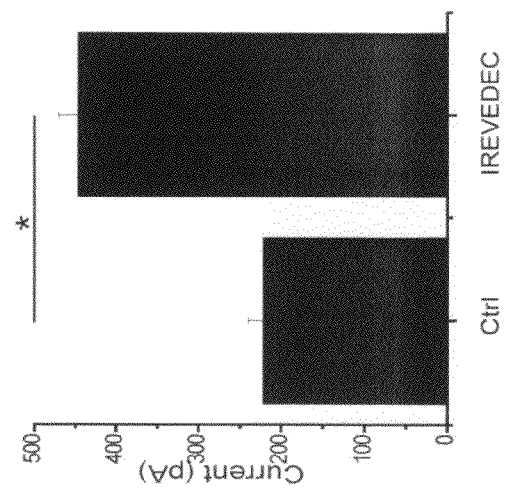
FIG. 7A
FIG. 7B

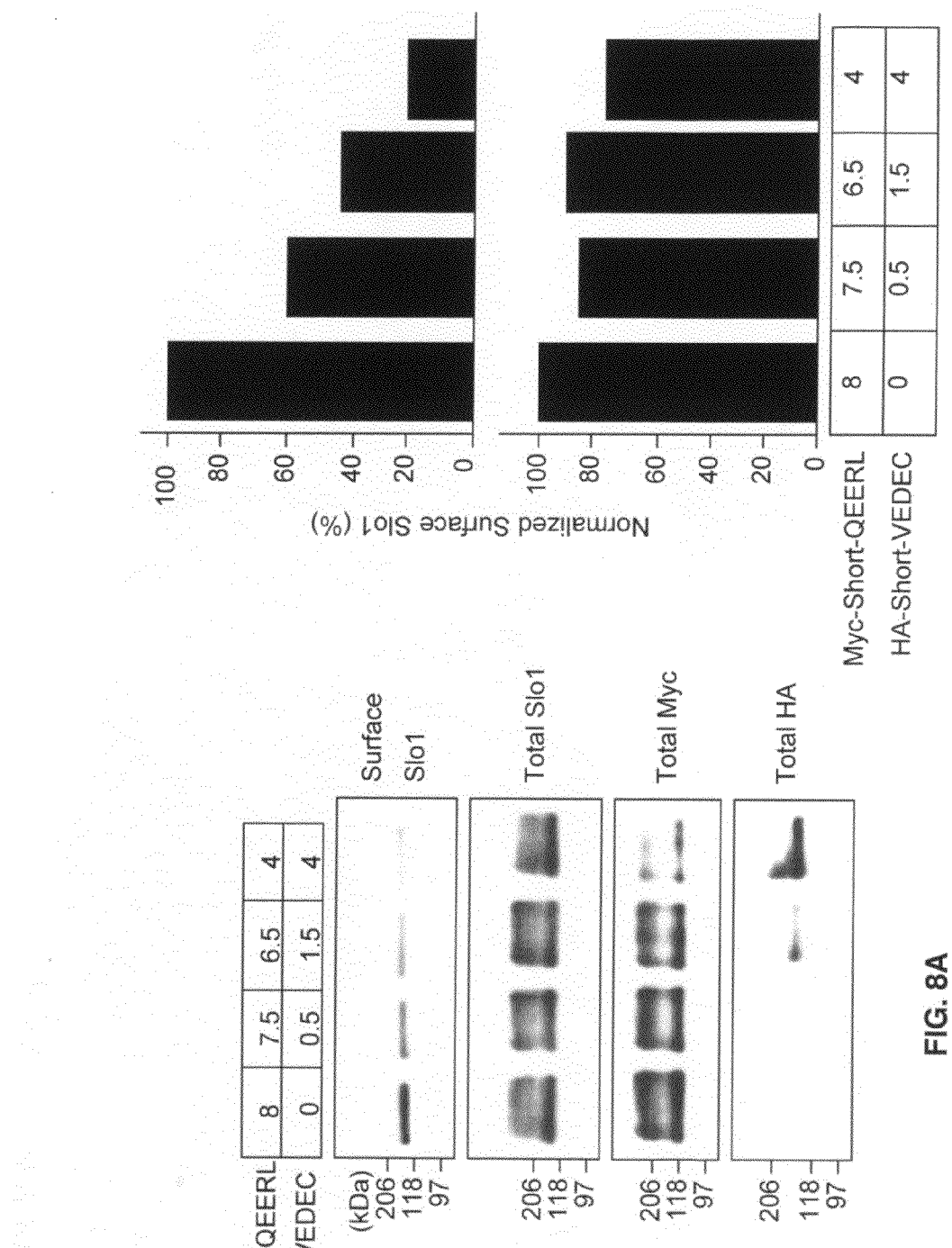

SEQUENCE LISTING

```
<160> NUMBER OF SEQ ID NOS: 20

<210> SEQ ID NO 1
<211> LENGTH: 27
<212> TYPE: DNA
<213> ORGANISM: Artificial sequence
<220> FEATURE:
<223> OTHER INFORMATION: right primer for ShortQEERL

<400> SEQUENCE: 1
atggatgcgc tcatcatacc ggtgacc                                           27

<210> SEQ ID NO 2
<211> LENGTH: 26
<212> TYPE: DNA
<213> ORGANISM: Artificial sequence
<220> FEATURE:
<223> OTHER INFORMATION: left primer for ShortQEERL

<400> SEQUENCE: 2
tgcgcccgct caaagccgct cttcct                                            26

<210> SEQ ID NO 3
<211> LENGTH: 27
<212> TYPE: DNA
<213> ORGANISM: Artificial sequence
<220> FEATURE:
<223> OTHER INFORMATION: right primer for ShortVEDEC

<400> SEQUENCE: 3
atggatgcgc tcatcatacc ggtgacc                                           27

<210> SEQ ID NO 4
<211> LENGTH: 30
<212> TYPE: DNA
<213> ORGANISM: Artificial sequence
<220> FEATURE:
<223> OTHER INFORMATION: left primer for ShortVEDEC

<400> SEQUENCE: 4
tcaacattca tcttcaacca cgtacttctg                                        30

<210> SEQ ID NO 5
<211> LENGTH: 30
<212> TYPE: DNA
<213> ORGANISM: Artificial sequence
<220> FEATURE:
<223> OTHER INFORMATION: right primer for LongVEDEC

<400> SEQUENCE: 5
ggtaccatgg atgcgctcat cataccggtg                                        30
```

-continued

<210> SEQ ID NO 6
<211> LENGTH: 29
<212> TYPE: DNA
<213> ORGANISM: Artificial sequence
<220> FEATURE:
<223> OTHER INFORMATION: left primer for LongVEDEC

<400> SEQUENCE: 6
tcaacattca tcttcaactt ctctgattg                              29

<210> SEQ ID NO 7
<211> LENGTH: 30
<212> TYPE: DNA
<213> ORGANISM: Artificial sequence
<220> FEATURE:
<223> OTHER INFORMATION: right primer for LongQEERL

<400> SEQUENCE: 7
ggtaccatgg atgcgctcat cataccggtg                             30

<210> SEQ ID NO 8
<211> LENGTH: 33
<212> TYPE: DNA
<213> ORGANISM: Artificial sequence
<220> FEATURE:
<223> OTHER INFORMATION: left primer for LongQEERL

<400> SEQUENCE: 8
tcaaagccgc tcttcctgtt ctctgattgg agg                         33

<210> SEQ ID NO 9
<211> LENGTH: 8
<212> TYPE: PRT
<213> ORGANISM: Artificial sequence
<220> FEATURE:
<223> OTHER INFORMATION: Octopetide modulator of Calcium activated
      Potassium channels

<400> SEQUENCE: 9

Ile Arg Glu Val Glu Asp Glu Cys
1               5

<210> SEQ ID NO 10
<211> LENGTH: 5
<212> TYPE: PRT
<213> ORGANISM: Artificial sequence
<220> FEATURE:
<223> OTHER INFORMATION: Peptide Modulator of Slo1 protein

<400> SEQUENCE: 10

Val Glu Asp Glu Cys
1               5

<210> SEQ ID NO 11
<211> LENGTH: 5
<212> TYPE: PRT
<213> ORGANISM: Artificial sequence
<220> FEATURE:
<223> OTHER INFORMATION: Peptide Modulator of Slo1 protein

<400> SEQUENCE: 11

Gln Glu Glu Arg Leu
1               5

<210> SEQ ID NO 12
<211> LENGTH: 5
<212> TYPE: PRT
<213> ORGANISM: Artificial sequence -continued

```
<220> FEATURE:
<223> OTHER INFORMATION: Conservative Mutant Of Peptide Modulator of
      Slo1 protein

<400> SEQUENCE: 12

Val Asp Asp Glu Cys
1               5

<210> SEQ ID NO 13
<211> LENGTH: 5
<212> TYPE: PRT
<213> ORGANISM: Artificial sequence
<220> FEATURE:
<223> OTHER INFORMATION: Conservative Mutant Of Peptide Modulator of
      Slo1 protein

<400> SEQUENCE: 13

Val Glu Glu Glu Cys
1               5

<210> SEQ ID NO 14
<211> LENGTH: 5
<212> TYPE: PRT
<213> ORGANISM: Artificial sequence
<220> FEATURE:
<223> OTHER INFORMATION: Conservative Mutant Of Peptide Modulator of
      Slo1 protein

<400> SEQUENCE: 14

Val Glu Asp Asp Cys
1               5

<210> SEQ ID NO 15
<211> LENGTH: 5
<212> TYPE: PRT
<213> ORGANISM: Artificial sequence
<220> FEATURE:
<223> OTHER INFORMATION: Conservative Mutant Of Peptide Modulator of
      Slo1 protein

<400> SEQUENCE: 15

Val Asp Asp Glu Cys
1               5

<210> SEQ ID NO 16
<211> LENGTH: 5
<212> TYPE: PRT
<213> ORGANISM: Artificial sequence
<220> FEATURE:
<223> OTHER INFORMATION: Conservative Mutant Of Peptide Modulator of
      Slo1 protein

<400> SEQUENCE: 16

Ile Glu Asp Glu Cys
1               5

<210> SEQ ID NO 17
<211> LENGTH: 5
<212> TYPE: PRT
<213> ORGANISM: Artificial sequence
<220> FEATURE:
<223> OTHER INFORMATION: Conservative Mutant Of Peptide Modulator of
      Slo1 protein

<400> SEQUENCE: 17

Ile Asp Asp Asp Cys
1               5
```

```
<210> SEQ ID NO 18
<211> LENGTH: 5
<212> TYPE: PRT
<213> ORGANISM: Artificial sequence
<220> FEATURE:
<223> OTHER INFORMATION: Conservative Mutant Of Peptide Modulator of
      Slo1 protein

<400> SEQUENCE: 18

Ile Glu Glu Glu Cys
1               5

<210> SEQ ID NO 19
<211> LENGTH: 5
<212> TYPE: PRT
<213> ORGANISM: Artificial sequence
<220> FEATURE:
<223> OTHER INFORMATION: Conservative Mutant Of Peptide Modulator of
      Slo1 protein

<400> SEQUENCE: 19

Ile Glu Asp Asp Cys
1               5

<210> SEQ ID NO 20
<211> LENGTH: 5
<212> TYPE: PRT
<213> ORGANISM: Artificial sequence
<220> FEATURE:
<223> OTHER INFORMATION: Conservative Mutant Of Peptide Modulator of
      Slo1 protein

<400> SEQUENCE: 20

Ile Asp Asp Asp Cys
1               5
```

SMALL PEPTIDE MODULATORS OF POTASSIUM CHANNEL TRAFFICKING

CROSS-REFERENCES TO RELATED APPLICATIONS

This nonprovisional application claims benefit of priority under 35 U.S.C. §119(e) of provisional U.S. Ser. No. 61/277,011, filed Sep. 18, 2009, now abandoned, the entirety of which is hereby incorporated by reference

BACKGROUND OF THE INVENTION

1. Field of the Invention

The present invention relates to the design, synthesis, and use of peptide modulators of ion channels. The peptides of the instant invention are useful in modulating ion-trafficking across potassium channels, specifically calcium activated potassium channels, such as BK and SK channels. More specifically, the present invention is drawn to the use of such peptide modulators in the treatments of pathophysiological conditions that are caused or characterized by electrolyte imbalances associated with calcium activated potassium channels.

2. Description of the Related Art

Large-conductance $Ca^{2+}$-activated $K^+$ channels ($BK_{Ca}$) channels whose α-subunits are encoded by the vertebrate Slo1 gene (which is also known as KCNMA1 and KCa1.1) are expressed in a wide range of tissues, including neurons and neuroendocrine cells, smooth muscle cells, endothelial and epithelial cells, and even in bone. The function of these channels is to cause cell hyperpolarization in response to physiological stimuli that elevate intracellular free $Ca^{2+}$ and that depolarize cells. $BK_{Ca}$ channels are often part of a negative feedback system that terminates $Ca^{2+}$ influx. As such, they can produce protective effects on cells that are damaged by prolonged elevations of intracellular $Ca^{2+}$. These channels also tend to cause relaxation of smooth muscles and general inhibition of the activity of other cell types by preventing their depolarization and by opposing $Ca^{2+}$ influx.

Functional $BK_{Ca}$ channels contain four pore-forming α-subunits. Each $BK_{Ca}$ α-subunit (Slo1 protein) has seven membrane-spanning α-helices with an extracellular $NH_2$ terminal domain, and a large globular cytopasmic COOH-terminal domain. $BK_{Ca}$ channels become active when $Ca^{2+}$ ions bind to specific sites on the cytoplasmic COOH-terminal domains of Slo1. Single-molecule measurements indicate that the opening of one $BK_{Ca}$ channel causes a membrane conductance of 180-200 pS when membranes are in symmetrical 150 mM KCl (a standard assay condition, but one that is not physiological).

The broad importance of $BK_{Ca}$ channels is highlighted by the phenotypes of knockout mouse models, which are mainly knockouts of the Slo1 gene and which have numerous defects including abnormal blood pressure control, altered endocrine status, deafness, alterations in smooth muscle and renal function, including bladder dysfunction, erectile dysfunction and abnormal electrolyte secretion by renal tubules, and several neurological problems. A Slo1 mutation in humans causes a coexistent generalized epilepsy and paroxysmal dyskinesia. On the basis of those observations, there is reason to believe that agents that increase the function of $BK_{Ca}$ channels could be therapeutically useful in conditions including but not limited to epilepsy, chronic pain, migraine, asthma, chronic obstructive pulmonary disease, urinary incontinence, hypertension, erectile dysfunction, irritable bowel syndrome, renal disorders of electrolyte imbalance, and possibly in certain kinds of cancer.

Proper trafficking of $BK_{Ca}$ channels is crucial and is a key regulatory step controlling their functional expression on the cell surface. This process is dependent on interactions of various protein binding partners with Slo1 variants inside cells, which regulate trafficking to the cell surface. In some tissues, for example brain and kidney $BK_{Ca}$ α-subunits (Slo1 proteins) occur in two general classes that differ at the extreme COOH-terminal. These include short forms that have been called $Slo1_{QEERL}$ (where QEERL=glutamine-glutamate-glutamate-argine-lysine) and long forms referred to as $Slo1_{VEDEC}$. The subscripts refer to the last five amino acid residues in each class of variants. $Slo1_{VEDEC}$ has a tail that extends 56 residues past the point where it diverges from $Slo1_{QEERL}$, and ends in the residues valine-glutamate-aspartate-glutamate-cysteine (VEDEC). The $Slo1_{QEERL}$ form extends an additional ends in glutamine-glutamate-glutamate-argine-lysine (QEERL). These splice variants result in channels that have very similar gating properties.

The $Slo1_{VEDEC}$ forms tend to be retained in intracellular storage pools and only move to the cell surface upon stimulation of the cells with appropriate hormones or growth factors. By contrast, $Slo1_{QEERL}$ is expressed constitutively at high levels on the surface of cells even without treatment by hormones or growth factors. $Slo1_{VEDEC}$ can exert a dominant-negative function on the trafficking of heteromeric channels in which it is present.

Previous pharmacological strategies for manipulating the function of $BK_{Ca}$ channels have been built around small molecules and natural-products/toxins that alter gating properties of channels or that affect the pore domains of the channel (primarily as inhibitors of ion flux). These effects are exerted on channels that are already localized at their normal positions in the cell membrane. There are limitations to this approach. Specifically, these molecules have tended to be non-specific in their actions, as they affect the gating of other types of channels, including calcium channels and chloride channels. Also, several have been reported to affect mitochondrial function and increase production of reactive oxygen species, and they are all lipophilic and therefore likely to cross the blood-brain barrier, resulting in a host of central effects that are likely to make the drugs poorly tolerated should they be used, for example, to treat erectile dysfunction.

Therefore, the purpose of the present invention is to overcome these limitations by designing, synthesizing, and testing small molecules that can affect the steady-state surface expression of $BK_{Ca}$ channels by regulating trafficking and/or stability in the membrane. This is a different mode of action that can be made more specific than existing known mechanisms, and therefore leads to improved therapeutic outcomes.

SUMMARY OF THE INVENTION

The present invention is directed to the design, synthesis, and use of peptide modulators of ion channel trafficking. Certain peptide modulators of the instant invention comprise an amino acid sequence of SEQ ID NO: 9. Certain peptide modulators comprise the amino acid sequence VEDEC (SEQ ID NO: 10) attached to the C-terminal end of the Slo1 protein isoform. In this sequence, V is valine, E is glutamate, D is aspartate, C is cysteine. The present invention teaches conservative mutants of VEDEC such as the sequences VDDDC (SEQ ID NO: 12), VEEEC (SEQ ID NO: 13), VEDDC (SEQ ID NO: 14), VDDEC (SEQ ID NO:15), IEDEC (SEQ ID NO:

16, wherein I is Isoleucine), IDDDC (SEQ ID NO: 17), IEEEC (SEQ ID NO:18), IEDDC (SEQ ID NO: 15), IDDEC (SEQ ID NO:20). The present invention also contemplates conjugations of the first valine that make the pentapeptide motif more membrane permeable, such as myristoyl moieties and arginine-rich cell penetrating peptides, such as HIV-TAT.

The present invention is drawn to treating a pathophysiological condition associated with electrolyte imbalance in an individual, that comprises administering to the individual a peptide modulator attached to the C-terminus of a SLO1 protein, such as the one described supra. Other applications of the peptide modulator are in the treatment of diseases/malfunctions, such as epilepsy, chronic pain, migraine, asthma, chronic obstructive pulmonary disease, urinary incontinence, hypertension, erectile dysfunction, irritable bowel syndrome, renal disorders of electrolyte imbalance, and possibly in certain kinds of cancer.

The present invention also contemplates methods of improving electrolyte balance across a cell membrane, comprising contacting the cell with a peptide modulator as described supra.

BRIEF DESCRIPTION OF THE FIGURES

FIG. 1A shows a schematic drawing of HA-tagged VEDEC (SEQ ID NO: 10) or QEERL (SEQ ID NO: 11) constructs (not to scale). From the top to the bottom: LongVEDEC, LongQEERL, ShortQEERL, and ShortVEDEC. White boxes represent the identical amino acid sequences in all Slo1 constructs. Gray boxes indicate the VEDEC-specific region, and the black boxes indicate the QEERL-specific region. The last five amino acids swapped are shown by letters. FIG. 1B depicts expressions of HA-tagged VEDEC (SEQ ID NO: 10)and QEERL (SEQ ID NO: 11) constructs. HEK293T cells are transiently transfected with the plasmids containing HA-tagged LongVEDEC, LongQEERL, ShortQEERL, or ShortVEDEC. Western blot analyses are performed and probed with antibodies as indicated.

FIGS. 2A-2E shows that ShortVEDEC has lower surface expression than ShortQEERL. FIG. 2A shows the representative result of cell-surface biotinylation assays performed in HEK293T cells heterologously expressing ShortQEERL and ShortVEDEC. The left lane is ShortQEERL, and the right lane is ShortVEDEC. Upper panel: the cell-surface expressed Slo1; lower panel: the total expression of Slot. FIG. 2B depicts the quantified results of the surface and total expressions of Slo1 compared to that of ShortQEERL. Data represent mean±S.E.M. from three separated experiments. Upper graph: normalized surface Slo1; lower graph: total expression of Slo1. FIG. 2C depicts whole-cell currents evoked at +60 mV (n=34, Mean±S.E.M.). Asterisk indicates a significant ($p<0.01$) difference between the current of ShortQEERL and ShortVEDEC. FIG. 2D shows representative traces of the whole-cell recording. Left is the ShortQEERL, and the right is the ShortVEDEC. X-axis scale: 100 ms; Y-axis scale: 500 pA. FIG. 2E is drawn to data representing mean±S.E.M. of $G/G_{max}$ of ShortQEERL (filled squares) and ShortVEDEC (filled circles) (n>11).

FIGS. 3A-3E show that LongQEERL has higher surface expression than LongVEDEC. FIG. 3A shows result of cell-surface biotinylation assays performed in HEK293T cells heterologously expressing LongVEDEC and LongQEERL. The left lane is LongVEDEC, and the right lane is LongQEERL. Upper panel: the cell-surface expressed Slo1; lower panel: the total expression of Slo1. FIG. 3B is drawn to quantified results of the surface and total expressions of Slo1 compared to that of LongVEDEC. Data represent mean±S.E.M. from three separated experiments. Upper graph: normalized surface Slo1; lower graph: total expression of Slo1. FIG. 3C shows whole-cell currents evoked at +60 mV (n=34, Mean±S.E.M.). Asterisk indicates the significant ($p<0.05$) difference between the current of LongVEDEC and LongQEERL. FIG. 3D is drawn to the representative traces of the whole-cell recording. Left is the LongVEDEC, and the right is the LongQEERL. X axis scale: 100 ms; Y axis scale: 500 pA. FIG. 3E depicts data representing mean±S.E.M. of $G/G_{max}$ of LongVEDEC (opened squares) and LongQEERL (opened circles) (n>11).

FIGS. 4A-4C are drawn to co-immunoprecipitation of VEDEC (SEQ ID NO: 10) and QEERL (SEQ ID NO: 11) in HKE293T cells. Lysates of HEK293T cells heterologously expressing Myc-tagged VEDEC (SEQ ID NO: 10) and HA-tagged QEERL (SEQ ID NO: 11) are immunoprecipitated with either mouse anti-Myc as shown in FIG. 4A or anti-HA antibodies as shown in FIG. 4B, and the normal mouse IgG served as the negative control. The immunoprecipitated Slo1 proteins are detected with mouse anti-HA or anti-Myc antibody as indicated. FIG. 4C depicts HA-tagged VEDEC (SEQ ID NO: 10) and Myc-tagged QEERL (SEQ ID NO: 11) are co-transfected in HEK293T cells. The co-expression of VEDEC (SEQ ID NO: 10)and QEERL (SEQ ID NO: 11) are shown by using confocal imaging. VEDEC (SEQ ID NO: 10) is detected with anti-HA antibodies (panels a and b) and QEERL (SEQ ID NO: 11) is probed with anti-Myc antibodies (panels c and d). Merged signals of VEDEC (SEQ ID NO: 10) and QEERL (SEQ ID NO: 11)are shown in panels e and f, and boxed regions in e and f are magnified in g and h, respectively.

FIGS. 5A-5B show that expression of VEDEC (SEQ ID NO: 10)reduces the surface expression of QEERL (SEQ ID NO: 11) and overall surface expression of Slo1 in a dose-dependent manner. HEK293T cells are transiently co-transfected with Myc-tagged QEERL (SEQ ID NO: 11) and HA-tagged VEDEC (SEQ ID NO: 10). The amounts of plasmids used are shown on the top of the figures. HA empty vectors are used to maintain the same amount of total plasmid used. FIG. 5A shows results from the representative cell-surface biotinylation assays. FIG. 5B depicts the total and surface expressions of Slo1 are quantified by densitometry and the normalized Slo1 expressions demonstrates the relative expression levels compared to that in cells expressing QEERL (SEQ ID NO: 11) only. Data represent means±S.E.M. from three different experiments.

FIGS. 6A-6D show IREVEDEC (SEQ ID NO: 9) peptides increase the surface expression of Slo1 channels transiently expressed in HEK293T cells. FIG. 6A and FIG. 6C show 1 mg R-PE (Ctrl) or IREVEDEC (SEQ ID NO: 9) delivered into HEK293T cells expressing $NH_2$-terminal Myc-tagged (ectofacial) $Slo1_{VEDEC}$ or $Slo1_{QEERL}$ by using PULSin reagent for 12 hours, which is followed by cell-surface biotinylation assays. The surface and total expression of $Slo1_{VEDEC}$ and $Slo1_{QEERL}$ are detected with anti-Myc. FIG. 6A and FIG. 6C are examples of representative cell-surface biotinylation assays. In FIG. 6B and FIG. 6D the surface (upper panel) and total (lower panel) expression of Slo1 are quantified by densitometry of the immunoblots. Data represent relative mean±S.E.M. from three different experiments. These data show that application of the IREVEDEC (SEQ ID NO: 9) peptide increases the surface expression of Slo1 I HEK293T cells expressing Myc-tagged $Slo1_{VEDEC}$ but has no effect on total cellular expression of this isoform (panel B). However, IREVEDEC (SEQ ID NO: 9) peptide has no effect on either the surface or the total expression of the Slo1$_{QEERL}$ form when it is expressed by itself (panel D).

FIGS. 7A-7B show that IREVEDEC (SEQ ID NO: 9) peptides increase functional activity of endogenous $Ca^{2+}$-activated $K^+$ channels in podocytes. FIG. 7A depicts whole cell recording analyses are carried out in differentiated mouse podocytes treated with either R-PE (control) or IREVEDEC (SEQ ID NO: 9) peptides. The recording electrode contained free $Ca^{2+}$ of 5 µM and currents are evoked by a series of depolarizing steps from a holding potential of −60 mV. Representative whole-cell current traces are shown above bar graphs Left: R-PE control (Ctrl); Right: IREVEDEC (SEQ ID NO: 9) peptides. FIG. 7B depicts a bar graph that shows mean±S.E.M. of current density at +60 mV with n=33 cells in each group. Asterisk indicates p<0.05.

FIGS. 8A-8B shows that the VEDEC (SEQ ID NO: 9) motif is sufficient to prevent Slo1 from being expressed on the cell surface. HEK293T cells were transiently co-transfected with Myc-tagged ShortQEERL and HA-tagged Short-VEDEC. FIG. 8A depicts results from representative cell-surface biotinylation assays as well as analyses of total expression of the HA and Myc tags. FIG. 8B shows quantification of densitometric analyses of three repetitions, showing reduction of surface expression of Slo1 when even small amounts of Short-VEDEC are present.

DETAILED DESCRIPTION OF THE INVENTION

Figure 1A:
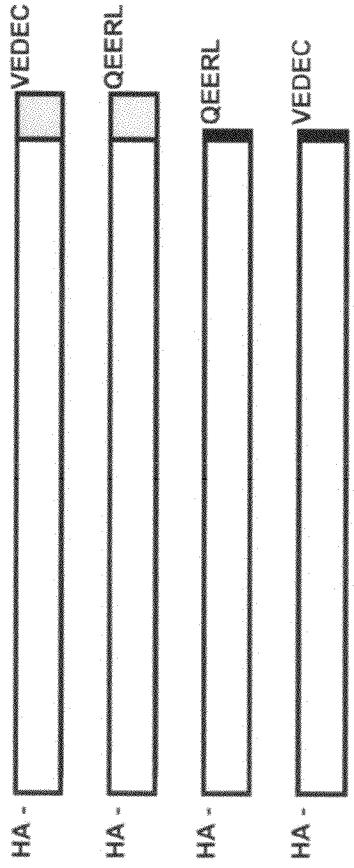
FIGS. 1A-1B depict motif-swapped constructs of VEDEC (SEQ ID NO: 10) and QEERL (SEQ ID NO: 11).

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); Sambrook, et al., Molecular Cloning: A Laboratory Manual (2nd Edition, 1989); Handbook of Surface and Colloidal Chemistry (Birdi, K. S. ed., CRC Press, 1997); Short Protocols in Molecular Biology, 4th ed. (Ausubel et al. eds., 1999, John Wiley & Sons); Molecular Biology Techniques: An Intensive Laboratory Course (Ream et al., eds., 1998, Academic Press); PCR (Introduction to Biotechniques Series), 2nd ed. (Newton & Graham eds., 1997, Springer Verlag); Peters and Dalrymple, Fields Virology, 2nd ed., Fields et al. (eds.) (B.N. Raven Press, New York, N.Y.).

All publications, patents and patent applications cited herein, whether supra or infra, are hereby incorporated by reference in their entirety.

As used herein the specification, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. Similarly, the word "or" is intended to include "and" unless the context clearly indicates otherwise. "Comprise" means "include." It is further to be understood that all base sizes or amino acid sizes, and all molecular weight or molecular mass values, given for nucleic acids or polypeptides are approximate, and are provided for description. Although methods and materials similar or equivalents to those described herein can be used in the practice or testing of the present disclosure, suitable methods and materials are described below. In case of conflict, the present specification, including explanations of terms, will control. In addition, the materials, methods, and examples are illustrative only and not intended to be limiting. Furthermore, unless otherwise required by context, singular terms shall include pluralities and plural terms shall include the singular.

The term "Ion Channel" as used herein refers to pore-forming proteins that help establish and control the small voltage gradient across the plasma membrane of all living cells by allowing the flow of ions down their electrochemical gradient. Because "voltage-activated" channels underlie the nerve impulse and because "transmitter-activated" channels mediate conduction across the synapses, channels are especially prominent components of the nervous system.

The term peptide, as used herein refers to any chain of amino acids, regardless of length or post-translational modification (e.g., glycosylation or phosphorylation).

As used herein, the term "subject" refers to any target of the treatment. Preferably, the subject is a mammal, more preferably, the subject is a canine or a human.

As used herein, the term "Cell penetrating peptides" (CPPs) are short peptides that facilitate cellular uptake of various molecular cargo (from small chemical molecules to nanosize particles and large fragments of DNA). The "cargo" is associated with the peptides either through chemical linkage via covalent bonds or through non-covalent interactions. The function of the cell penetrating peptides are to deliver the cargo into cells, a process that commonly occurs through endocytosis with the cargo delivered to the endosomes of living mammalian cells. One example of said cell penetrating peptides is the trans-activating transcriptional activator (HIV-Tat) from Human Immunodeficiency Virus 1 (HIV-1).

The present invention is directed the design, synthesis, and use of peptide modulators of ion channel trafficking. Certain peptide modulators of the instant invention comprise an amino acid sequence of SEQ ID NO: 9. Certain peptide modulators comprise the amino acid sequence VEDEC (SEQ ID NO: 10) attached to the C-terminal end of the Slo1 protein isoform. The present invention teaches conservative mutants of VEDEC such as the sequences VDDDC (SEQ ID NO: 12), VEEEC (SEQ ID NO: 13), VEDDC (SEQ ID NO: 14), VDDEC (SEQ ID NO: 15), IEDEC (SEQ ID NO: 16, wherein I is Isoleucine), IDDDC (SEQ ID NO: 17), IEEEC (SEQ ID NO:18), IEDDC (SEQ ID NO: 19), IDDEC (SEQ ID NO: 20). The present invention also claims conjugations of the peptide modulator that render said modulator more membrane permeable, such as myristoyl moieties and arginine-rich cell penetrating peptides, such as HIV-TAT.

The present invention is drawn to treating a pathophysiological condition associated with electrolyte imbalance in an individual, comprising: administering to the individual a peptide modulator attached to the C-terminus of a SLO1 protein. Other applications of the peptide modulator are in the treatment of diseases/malfunctions such as epilepsy, chronic pain, migraine, asthma, chronic obstructive pulmonary disease, urinary incontinence, hypertension, erectile dysfunction, irritable bowel syndrome, renal disorders of electrolyte imbalance, and possibly in certain kinds of cancer. The present invention also contemplates methods of improving electrolyte balance across a cell membrane, comprising contacting the cell with the peptide modulators of the instant invention.

In a preferred embodiment, the present invention is drawn to treating a pathophysiological condition associated with electrolyte imbalance in an individual, said method comprising administering to the individual a peptide modulator attached to the C-terminus of a SLO1 protein, wherein said peptide modulator comprises a sequence shown in SEQ ID NO: 10 or a conservative mutation thereof shown in SEQ ID NO: 12-SEQ ID NO: 20.

The present invention is comprised of peptide modulators based on the following amino acid sequences: V-E/D-E/D-E/D-C, where V is valine, E is glutamate, D is aspartate and C is cysteine and E/D can be either glutamate or aspartate. Such peptide modulators are attached to the end of a Slo1 protein to significantly improve ion trafficking through $Ca^{2+}$-activated potassium channels. The present invention also includes conjugations of the first valine that make the pentapeptide motif more membrane permeable, such as myristoyl moieties and arginine-rich cell penetrating peptides.

The approach described herein is mechanistically unique as it offers the advantage of occurring in a more restricted subset of tissues, that is particularly those that express the $Slo1_{VEDEC}$ isoform.

It is shown herein that:
1) The presence of the VEDEC motif at the end of a Slo1 protein is sufficient to suppress surface expression of either the long or short forms of Slo1;
2) $Slo1_{VEDEC}$ and $Slo1_{QEERL}$ form heteromers;
3) Heteromeric Slo1 proteins that contain a VEDEC motif at the COOH-terminal tail, possibly even those with only a single $Slo1_{VEDEC}$ subunit, show reduced trafficking to the surface; and
4) The VEDEC motif provides a pharmacological basis for increasing surface expression of Slo1 proteins, since treating cells with relatively short peptides (8-24 residues) that contain the VEDEC motif increases the surface expression of heterologously and endogenously expressed $BK_{Ca}$ channels.

EXAMPLE 1

Plasmid Constructs

The constructs (FIG. 1) encoding HA-tagged Short-QEERL and ShortVEDEC were PCR amplified by using Myc-tagged QEERL as the template and the following primers: 5'-ATGGATGCGCTCATCATACCGGTGACC-3'/5'-TGCGCCCGCTCAAAGCCGCTCTTCCT-3' (Short-QEERL-SEQ ID NOS: 1-2), 5'-ATGGATGCGCTCATCATACCGGTGACC-3'/5'-TCAACATTCATCTTCAACCACGTAC TTCTG-3' (ShortVEDEC-SEQ ID NOS: 3-4). The PCR products were ligated with pCR2.1 (Invitrogen), and then, subcloned into pCMV-HA (Clontech, with KpnI and NotI digestion). The constructs encoding LongVEDEC and LongQEERL were PCR amplified by using the Myc-tagged VEDEC as the template with the following primers: 5'-GGTACCATGGATGCGCTCATCATACCGGTG-3'/5'-TCAACATTCATCTTCAACTTCTCTGATTG-3' (LongVEDEC-SEQ ID NOS: 5-6), 5'-GGTACCATGGATGCGCTCATCATACCGGTG-3'/5'-TCAAAGCCGCTCTTCCTGTTCTCTG ATTG-GAGG-3' (LongQEERL-SEQ ID NOS: 7-8). The PCR products were ligated with pCR2.1, and then, subcloned into pCMV-HA with KpnI sites. The sequences of these constructs were confirmed by sequencing analyses.

EXAMPLE 2

Cell Culture and Transfection

HEK293T (human embryonic kidney) cells were grown in Dulbecco's modified Eagle's medium (Invitrogen) containing heat-inactivated 10% fetal bovine serum (FBS) and penicillin-streptomycin (Invitrogen) at 37° C. in a 5% $CO_2$ incubator. Cells were transiently transfected for 24 to 48 hours using Lipofectamine 2000 (Invitrogen) in the serum-reduced medium OPTI-MEM, Invitrogen) following the manufacturer's instructions. The immortalized and undifferentiated mouse podocyte cell line was grown in RPMI1640 with 10% FBS supplied with 10 U/mL interferon-g (INF-γ) at 33° C. in a 5% $CO_2$ incubator. Podocytes' differentiation was induced by removing INF-γ and switching to 37° C. in a 5% $CO_2$ incubator for 14 days.

EXAMPLE 3

Cell-Surface Biotinylation, Co-Immunoprecipitation, and Immunoblo Analysis

Cell-surface biotinylation was carried out by labeling cells with 1 mg/mL EZ-Link Sulfo-NHS-Biotin reagents (Pierce) in PBS (137 mM NaCl, 10 mM Phosphate, 2.7 mM KCl, pH 7.4) at 4 C with gentle shaking for 1.5 hours, which was followed by incubating the labeled cells in the cold PBS containing 100 mM glycine for additional 20 minutes at 4° C. to stop the reaction. Cells were lysed by PBS containing 0.5% Triton X-100 (Sigma) and protease inhibitors (Sigma). Cell lysates were centrifuged and the supernatants are collected. A portion of the supernatants was reserved as samples of the total expression of Slo1. The biotinylated proteins from the cell surface were recovered from the remainder of the lysates by incubating with immobilized strepavidin-agarose beads (Pierce) at 4 C for 2 hours. Beads were washed by PBS and collected by centrifugation, and then boiled in the Laemmli buffer (50% glycerol, 10% SDS, 10% 2-mercaptaethonal, Tris 50 mM, 0.02% bromphenol blue, 5×).

For immunoprecipitation, cells were lysed and supernatants were collected as described above. Cell lysates with 500 mg total proteins were incubated in the presence of mouse anti-Myc (9B11, Cell signaling) or anti-HA antibodies (6E2, Cell signaling) at 4° C. After 4 hours of incubation, protein A/G agarose beads (Santa Cruz Biotechnology) were added to the lysates, which were kept at 4° C. for another 16 hours with gentle shaking. Beads were extensively washed by PBS and collected by centrifugation, and then, boiled in the Laemmli buffer.

All samples were loaded and separated on 10% SDS-PAGE. Proteins were transferred to nitrocellulose papers followed by blocking in 5% nonfat dried milk dissolved in TBST buffer (10 mM Tris, 150 mM NaCl, and 0.1% Tween 20, pH 7.4). Slo1 proteins were detected by primary antibodies, including mouse anti-Myc, mouse anti-HA, rabbit anti-VEDEC, rabbit anti-QEERL, and rabbit anti-Slo1 (APC107, Alomone labs) antibodies, as indicated. Horseradish peroxidase (HRP)-conjugated secondary antibodies (Cell Signaling) and SuperSignal West Pico Chemiluminescent Substrate (Thermo Scientific) were used, and immunoreactive bands were visualized by using autoradiography films. Results were scanned and processed by ImageJ (NIH) to determine the intensities of signals.

EXAMPLE 4

Electrophysiology

Whole cell recordings were performed in HEK293T transiently expressing different Slo1 constructs using standard methods. The bath solution contains (in mM) NaCl 150, KCl 0.08, MaCl$_2$ 0.8, CaCl2 5.4, glucose 10, Hepes 10, and pH was adjusted to 7.4 with NaOH. The pipette solution contains (in mM) NaCl 145, KCl 2, MgCl$_2$ 6.2, CaCl$_2$ 5 mM, pH 7.2. Because HEK293T cells do not express endogenous Ca$^{2+}$ current, the pipette solution provided sufficient Ca$^{2+}$ to activate BK$_{Ca}$ channels while keeping macroscopic currents small enough to avoid saturation the patch-clamp amplifier. Whole cell currents were evoked by a series of eight 450-ms depolarizing steps (from −25 mV to +80 mV in 15 mV increments) from a holding potential of −60 mV.

EXAMPLE 5

Peptide Delivery

The octopetide, NH$_2$-IREVEDEC-COOH (SEQ ID NO: 9), was synthesized by Peptide 2.0 (Chantilly, Va.). For the cell surface biotinylation assay, HEK293T cells in 6-well tissue culture plates were transiently transfected with Slo1 by using Lipofectamine-2000 as described above. After 30 hours of incubation, transfected cells were washed by PBS and then incubated with the mixture of IREVEDEC peptide and PULS in peptide delivery reagent (PolyPlus, NY) according to manufacturer's instruction. Briefly, 1 mg octopeptides were diluted in 200 mL HEPES buffer which was followed by adding 12 mL PULSin reagents. The mixture was added to the trasfected cells cultured in 2.8 mL DMEM per well after being incubated at the room temperature for 15 minutes. The same amount of R-phycoerythrin (R-PE) provided by the manufacturer was used as a negative control. After 4 hours of incubation, media containing the mixture was removed and cells were grown in regular media for another 12 hours. For the whole-cell recording, differentiated mouse podocytes were seeded on coverslips coated with type I collagen and peptide delivery was performed by using 3 mg octopeptide and 12 mL PULSin in 2.8 mL of culture medium.

EXAMPLE 6

Endocytosis Assay

HEK293T cells were seeded at 30% confluence in 12-wells 24-hr before transfection. Cells heterogeneously expressing Myc-tagged VEDEC (SEQ ID NO: 10) or QEERL (SEQ ID NO: 11) were placed at 4° for 20 min to stop channel trafficking and degradation. Surface Slo1 was labeled with mouse anti-Myc antibodies in cold medium at 4° for 1 hr. After an extensive wash with cold media, trafficking was allowed to resume by incubating cells at 37° C. for different periods of time. Cells were fixed by PBS containing 4% paraformaldehyde (Sigma) without being permeablized. The anti-Myc antibodies remaining on the cell surface were detected using HRP-conjugated anti-mouse IgG antibodies and then exposed to FAST OPD™ reagents (Sigma) for 3 min with constant shacking. The colorimetric reaction was stopped by adding 3 N HCl for 10 min at room temperature. The supernatant was collected and the optical absorbance was measured at 492 nm by using a Multiskan MCC microplate reader (Fisher Scientific).

EXAMPLE 7

Immunocytochemistry and Confocal Microscopy

HEK293T cells heterologously co-expressing HA-tagged VEDEC and Myc-tagged QEERL were fixed at room temperature for 10 minutes by using 4% paraformaldehyde in PBS. Fixed cells were permeablized blocked with PBS containing 0.5% Triton X-100 and 5% BSA at 37° C. for 1 hr. Cells were incubated in PBS containing rabbit anti-Myc antibodies (1:250, Upstate) and mouse anti-HA antibodies (1:250, Cell Signaling) with additions of 0.3% Triton X-100 and 3% BSA for 1 hour at 37° C. After 3 times of wash with PBS, primary antibodies were probed with Alexa Flour 568 conjugated anti-mouse IgG antibodies (1:1000, Molecular Probes) and Alexa Flour 488 conjugated anti-rabbit IgG antibodies (1:1000, Molecular Probes), which were diluted in PBS containing 0.3% Triton X-100 and 3% BSA, for 1 hour at 37° C. Cells were rinsed and mounted. All images were taken on the Olympus FV-1000 inverted stage confocal microscope using a Plan Apo N 60× 1.42NA oil-immersion objective, and processed by FluoView software (Olympus).

EXAMPLE 8

Data Collection and Analysis

All quantitative data are presented as mean±S.E.M. Data was analyzed by Student's t-test with p<0.05 was considered as significant.

EXAMPLE 9

Figure 1B:
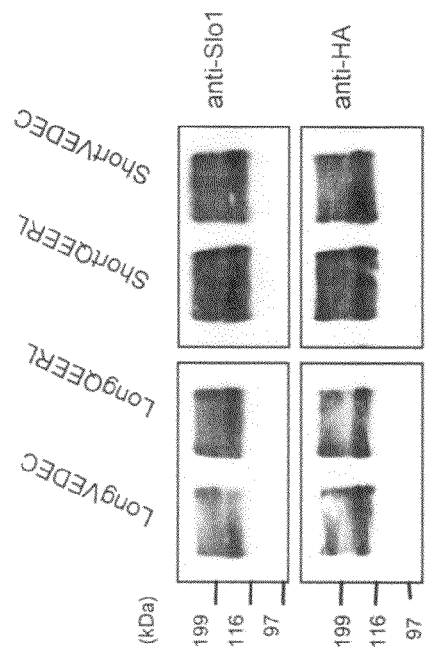

Motif-Swapped Constructs Reveal a Significant Role for the Last Five Residues of Slo1 Splice Variants The wild-type Slo1$_{VEDEC}$ and the wild-type Slo1$_{QEERL}$ variants that were used herein are identical for their first 1108 residues. The Slo1$_{QEERL}$ form has a short tail that extends 8 residues past the point where the two forms diverge, whereas Slo1$_{VEDEC}$ has a long COOH-terminal tail that extends for 61 residues past the point where the isoforms diverge. In principle, a signal that leads to retention of Slo1$_{VEDEC}$ in intracellular compartments could lie anywhere within that unique 61-residue tail. To test whether the essential portion occurs at the very end of the molecules, constructs encoding a series of HA-tagged Slo1 proteins in which the last five residues were switched were prepared. These constructs are shown schematically in FIG. 1A, and include Slo1 channels with the long tail ending in VEDEC (the wild-type long form, hereafter called Long-VEDEC) and a motif-swapped version that was identical except that it ends in QEERL (hereafter called Long-QEERL). Slo1 channels with short COOH-terminal tails that end in QEERL (the wild-type short form, hereafter referred to as Short-QEERL) and a switched version that ends in VEDEC (Short-VEDEC) were also prepared. These constructs were confirmed by sequencing, and detected their expression in HEK293T cells by immunoblot analysis using either anti-HA or anti-Slo1 (FIG. 1B). The cell-surface expression of these COOH-terminal wild-type and motif-switched Slo1 variants were examined by means of cell-surface biotinylation assays and whole-cell recordings in HEK293T cells (FIGS. 2 and 3). Although Short-QEERL and Short-VEDEC show similar levels of total expression, the surface expression of Short-VEDEC was markedly reduced compared to that of Short-QEERL (FIGS. 2A, 2B).

Consistent with these results, the whole-cell current recorded from cells expressing Short-VEDEC was also significantly reduced compared to Short-QEERL (FIGS. 2C, 2D). Note that in these recordings the recording electrodes contained a saline in which the free $Ca^{2+}$ was buffered to 5 μM and currents were evoked by application of a series of depolarizing voltage steps. Swapping VEDEC (SEQ ID NO: 10) for QEERL (SEQ ID NO: 11) at the end of the short Slo1 isoform causes a very modest right-shift in the voltage-dependence of activation at these voltages (FIG. 2E). However, this shift cannot account for the marked difference in currents observed, meaning that the main effect was due to the number of Slo1 channels on the cell surface available for activation. A higher surface expression of Long-QEERL compared to Long-VEDEC (FIGS. 3A and 3B) was observed, which was also reflected in comparable differences in whole-cell current (FIGS. 3C and 3D) that cannot be attributed to changes in the voltage-dependence of activation (FIG. 3E).

Whether the VEDEC motif can account for dominant-negative effects on Slo1 trafficking observed with co-expression of Slo1$_{VEDEC}$ was examined. Therefore, HEK293T cells were transfected with combinations of the Short-QEERL and Short-VEDEC constructs (which differ only in the last five residues) and surface expression of total Slo1 proteins was examined. The presence of the VEDEC motif in only a small portion of the proteins expressed was sufficient to cause robust suppression of Slo1 (FIG. 8A-8B). These data strongly support the hypothesis that the VEDEC and/or QEERL motifs are involved in regulating the trafficking of Slo1 channels into or out of the cell surface.

EXAMPLE 10

Biochemical Interactions Between Slo1$_{VEDEC}$ and Slo1$_{QEERL}$

Functional $BK_{Ca}$ channels are minimally comprised of four Slo1 proteins, although auxiliary β-subunits are usually present in endogenous channels. It is shown herein that the Slo1$_{VEDEC}$ and Slo1$_{QEERL}$ isoforms interact biochemically in a heterologous expression system. This was done by transiently transfected HEK293T cells with plasmids that encode $NH_2$-terminal (ectofacial) HA-tagged Slo1$_{QEERL}$ and Myc-tagged Slo1$_{VEDEC}$ and then carried out co-immunoprecipitation. Using immunoblot analysis, both HA and Myc were detected in precipitates when Slo1 was immunoprecipitated with either anti-Myc (FIG. 4A) or anti-HA (FIG. 4B). Neither tag was detected when the initial immunoprecipitation was carried out with rabbit IgG. Consistent with these results, partial co-localization of Slo1$_{VEDEC}$ and Slo1$_{QEERL}$ was observed by confocal microscopy as illustrated in FIG. 4C, using antibodies against the Myc and HA tags (FIG. 4B) showing that a portion of the Slo1 proteins expressed in these cells are heteromeric.

EXAMPLE 11

Co-Expression of Slo1$_{VEDEC}$ Suppresses the Steady-State Surface Expression of Slo1$_{QEERL}$ It is well established that Slo1$_{QEERL}$ is normally expressed at relatively high levels on the cell surface, whereas Slo1$_{VEDEC}$ is largely retained in intracellular pools. This raises the question as to how heteromeric Slo1 proteins might behave with respect to their expression on the cell surface. To address this, cell-surface biotinylation assays were carried out on HEK293T cells transiently expressing HA-Slo1$_{VEDEC}$ and Myc-Slo1$_{QEERL}$ in different ratios (FIG. 5A). These assays were quantified by densitometry (FIG. 5B). In these experiments, the total amount of Slo1-encoding plasmid transfected into cells was the same in each group, which causes the total amount of Slo1 in the HEK293T cells to be constant as measured by immunoblot analysis of total cell lysates using anti-Slo1.

While the total expression of Slo1 proteins remains the same in all groups of cells, the percentage that was on the cell surface was markedly decreased with even a modest increase of Slo1$_{VEDEC}$ expression relative to Slo1$_{QEERL}$. Thus, a 50% reduction in mean surface expression of Slo1 was observed when only 12.5% of the DNA transfected into the cells encoded Slo1$_{VEDEC}$, and 87.5% encoded Slo1$_{QEERL}$ (FIG. 5B). These data show that Slo1$_{VEDEC}$ has a dominant-negative effect on the steady-state expression of Slo1 proteins on the cell surface.

EXAMPLE 12

VEDEC Peptides Promote the Cell Surface Expression of Slo1

Two different approaches to introduce highly acidic peptides into the cytosol are used herein. In the first set of experiments, the octopeptide IREVEDEC (SEQ ID NO: 9) was synthesized and delivered into HEK293T cells expressing full-length Slo1$_{VEDEC}$ or Slo1$_{QEERL}$ using a commercially available proprietary reagent called PULSin™. A similar amount of R-phycoerythrin (R-PE) was introduced into control HEK293T cells which also served to assess the efficiency of the peptide delivery system. The effect of these treatments on Slo1 was examined using cell-surface biotinylation assays carried out in HEK293T cells heterologously expressing either Myc-Slo1$_{VEDEC}$ or Myc-Slo1$_{QEERL}$.

Delivery of IREVEDEC has no effect on the total expression of either Slo1 isoform as shown in FIGS. 6A, 6C. However, the IREVEDEC octopeptide increases the surface expression of Slo1$_{VEDEC}$ compared to that observed in the R-PE control (FIG. 6A). By contrast, IREVEDEC treatment has no effect on the surface expression of Slo1$_{QEERL}$ (FIG. 6D). A second approach was used to examine functional consequences of IREVEDEC peptides for Slo1 type channels expressed endogenously. This was measured using whole-cell recordings from mouse podocytes. IREVEDEC treatment caused a large increase in current through $Ca^{2+}$-activated $K^+$ channels in these cells. Examples of representative recordings of whole-cell current are shown in FIG. 7A. The effect of IREVEDEC on podocyte $BK_{Ca}$ currents was statistically significant as shown in FIG. 7B. Moreover, the IREVEDEC treatment does not alter the activation or deactivation kinetics of macroscopic currents (data not shown). Podocytes naturally express $BK_{Ca}$ channels and they therefore represent a highly physiological assay. The data in FIG. 7 therefore show that short peptides containing the VEDEC can have a large effect on the functional expression of endogenously expressed $BK_{Ca}$ channels and actually lead to an increase in current flowing into cells under conditions where these channels become active, and that they do with this without changing the gating properties of channels that are already in the plasma membrane.

EXAMPLE 13

Similar Inward Trafficking Slo1$_{VEDEC}$ and Slo1$_{QEERL}$

The steady-state surface expression of a membrane protein was determined by the rates and balance of movements into and out of the plasma membrane. While the presence of the VEDEC motif in Slo1 reduces constitutive steady-state expression on the cell surface, the available data do not indicate how the VEDEC motif produces this effect. To examine this, HEK293T cells were transiently transfected with either Myc-Slo1$_{QEERL}$ or Myc-Slo1$_{VEDEC}$. After 48 hr, the Slo1 proteins on the cell surface were labeled with mouse anti-Myc at 4° C., and inward trafficking was then monitored by bring the cells back to 37° C. for different periods of time. The anti-Myc antibodies remaining on the cell surface were labeled with HRP-conjugated anti-mouse IgG and quantified using a colorimetric assay that measured absorbance at 492 nm. In these experiments, the amounts of total expression of Slo1$_{QEERL}$ and Slo1$_{VEDEC}$ determined by immunoblot analysis were indistinguishable (data not shown).

Figure 9:
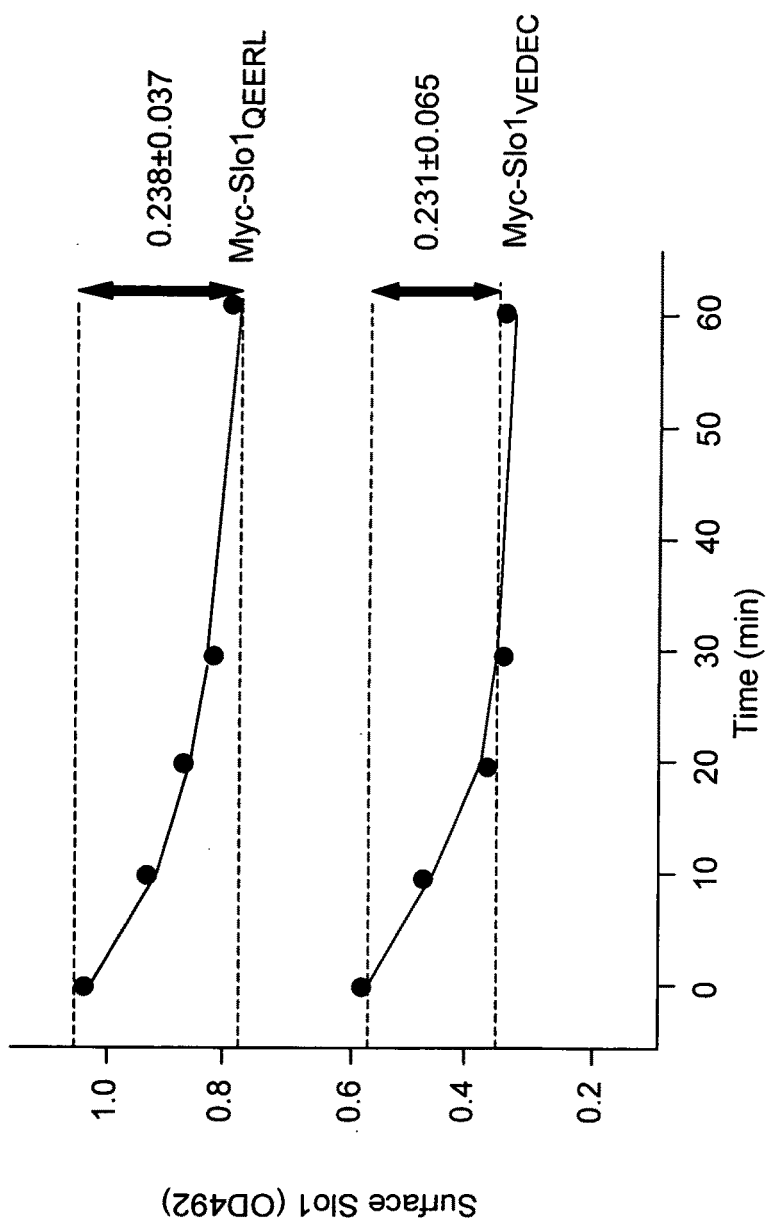
FIG. 9 shows time course of Slo1$_{VEDEC}$ and Slo1$_{QEERL}$ removal from the cell surface. Endocytosis assays were carried out by using HEK293T cells heterologously expressing either Slo1$_{VEDEC}$ or Slo1$_{QEERL}$. The expressed channels bear an Myc tag at the extracellular $NH_2$ terminus, which allowed surface Slo1 on the surface of intact cells to be labeled by anti-Myc at 4° C. Cells were then placed at 37° C. for various times to allow trafficking to resume, at which time they were fixed. The amounts of anti-Myc remaining on the cell surface were determined by HRP-conjugated anti-mouse with colorimetric assays at $OD_{492}$. Data are fitted with single-exponential decay functions with time constants of 15.1±0.9 (for Slo1$_{QEERL}$) and 14.4±3.4 min (for Slo1$_{VEDEC}$).

Based on this colorometric assay, the total amount of Slo1$_{QEERL}$ on the cell surface was greater than that of Slo1$_{VEDEC}$ at the time at which cells were transferred back to 37° (t=0), which was consistent with all other methods that we have used to analyze steady-state expression. Both Slo1 isoforms showed a subsequent exponential decline in cell surface expression over time that reached a new steady-state by 60 min, and the rate of internalization was indistinguishable for the two forms (FIG. 9). Specifically, the optical signal for Slo1$_{VEDEC}$ declined with a time-constant of 14.4±3.4 min and the steady-state decline of the signal (measured after 60 min) was 0.231±0.065 optical density units (ODU$_{492}$). Signal for Slo1$_{QEERL}$ declined with a time-constant of 15.1±0.9 min and the steady-state decline after 60 min was 0.238±0.037 ODU$_{492}$ (FIG. 9). These data suggest that the inward trafficking of both splice variants was carried out by similar mechanisms that have indistinguishable capacities and kinetics in HEK293t cells. Therefore, the effects of the VEDEC motif are exerted on forward trafficking.

Discussion

In the present study, it has been shown that two different COOH-terminal splice variants of Slo1, known as Slo1$_{VEDEC}$ and Slo1$_{QEERL}$, are able to form heteromeric channels in a heterologous expression system. This is not surprising because both isoforms contain the tetramerization domain located between S6 and S7 that was identified by Quirk and Reinhart (2001), and this domain is present in all Slo1 splice variants. Nevertheless, formation of this particular heteromeric complex has important functional consequences, confirming an earlier report (1) that Slo1$_{VEDEC}$ can function as a dominant-negative subunit for the steady-state expression of heteromeric channels to the cell surface, probably as a result of its binding to an as yet unidentified protein that traps the complex in intracellular compartments. This conclusion is supported by the observation that intracellular delivery of two small peptides that contain the VEDEC motif, IREVEDEC and Pene-VEDEC, is able to increase surface expression of heterologously and endogenously expressed Slo1 channels. It bears noting that the VEDEC motif is the only sequence element that these two small peptides have in common.

It has been shown that Slo1$_{QEERL}$ shows robust constitutive expression on the cell surface, whereas Slo1$_{VEDEC}$ is preferentially maintained in intracellular compartments, at least until cells are stimulated with certain growth factors or in the presence of certain Slo1-interacting proteins (1-3). The present data attribute these differences in the behavior of the splice variants to small pentapeptide motifs at the extreme COOH-termini of Slo1, a conclusion that is supported by examining the behavior of constructs in which only the last five residues are changed. Thus, Slo1 channels that end in the VEDEC motif have reduced surface expression regardless of whether they end in long or short COOH-terminal tails.

The present study also provides evidence that Slo1$_{QEERL}$ and Slo1$_{VEDEC}$ are removed from the cell surface of HEK293T cells to a similar extent and by similar kinetics, at least over a period of 60 minutes. The data suggest that the difference in the constitutive surface expression of Slo1$_{VEDEC}$ and Slo1$_{QEERL}$ is primarily due to differences in their rates of forward trafficking into the plasma membrane. It has been previously shown that Slo1$_{VEDEC}$ and Slo1$_{QEERL}$ are endogenously expressed in the same cell populations including chick ciliary ganglion neurons and mouse podocytes. The role of growth factor signaling cascades in regulation of the steady-state surface expression of Slo1 in chick ciliary ganglion neurons is examined. In those cells, the surface expression of Slo1 is regulated by at least two different growth factors that signal through PI$_3$ kinase cascades. Data suggests the presence of regulated trafficking of endogenous Slo1 channels in podocytes as well. A similar type of regulation will occur in any cell type that expresses Slo1$_{VEDEC}$, regardless of which Slo1 variants may be co-expressed.

The VEDEC motif is similar to type III PDZ-binding motifs, which are most typically found as the terminal sequence of proteins, and which have been shown to affect the trafficking and stability of other types of ion channels (4-7). In this regard, Slo1$_{VEDEC}$ binds to one of the PDZ-domains of a scaffolding protein known as MAGI-1, which causes Slo1 to be sequestered in intracellular compartments in several cell types. While this would appear to be a promising candidate for a VEDEC-binding protein, it has also been observed that MAGI-1 produces a similar effect on Slo1$_{QEERL}$, as well as on a third COOH-terminal variant known as Slo1$_{EMVYR}$, and can biochemically interact with all three COOH-terminal Slo1 variants. Thus, MAGI-1 is probably not responsible for the different trafficking behaviors of extreme COOH-terminal variants of Slo1, at least not by itself. In addition, these results suggests a mechanism for Slo1$_{VEDEC}$-interacting proteins such as BK$_{Ca}$ α-subunits (2), filamin-A, α 1 subunits of Na$^+$-K$^+$-ATPase, and nephrin (8), which interact with the distal COOH-terminal and stimulate surface expression of Slo1$_{VEDEC}$. Interactions with these proteins sterically inhibit access of the VEDEC motif to other proteins that suppress Slo1 expression on the cell surface. This provides a basis for dynamic regulation of Slo1 expression based on protein interactions that change over time.

In summary, it has been shown that a pentapeptide motif at the extreme COOH-terminal of Slo1$_{VEDEC}$ proteins is sufficient to impede constitutive trafficking of complexes containing this motif to the cell surface. Small peptides that contain this motif are able to stimulate expression of functional BK$_{Ca}$ channels on the cell surface, and suggest new pharmacological strategies for increasing BK$_{Ca}$ function in cells.

References

1. Ma D, et al. FEBS Lett (2007) 581:1000-1008.
2. Kim E Y, et al. J Neurophysiol (2007) 97:3508-3516.
3. Kim E Y, et al. Neuroscience (2007) 146:1652-1661.
4. Maximov A, Sudhof T C, Bezprozvanny I (1999) J Biol Chem 274:24453-24456.
5. Okabe S, Miwa A, Okado H. J Neurosci (1999) 19:7781-7792.
6. Standley S, et al. Neuron (2000) 28:887-898.
7. Duggan A, et al. J Biol Chem (2002) 277:5203-5208.
8. Kim E Y, et al. Am J Physiol Renal Physiol (2008) 295: F235-246.
9. Butler A, et al. Science (1993) 261:221-224.
10. Dhulipala P D, Kotlikoff M I. Biochim Biophys Acta (1999) 1444:254-262.
11. Ghatta S, et al. Pharmacol Ther (2006) 110:103-116.
12. Beisel et al. Gene (2007) 386:11-23.
13. Brenner R, et al. Nature (2000) 407:870-876.
14. Kim E Y, et al. Mol Pharmacol (2009) 75:466-477.
15. Kundu P, et al. J Biol Chem (2007) 282:27478-27492.
16. Kwon S H, Guggino W B. Proc Natl Acad Sci USA (2004) 101:15237-15242.

17. Lu R, Alioua A, Kumar Y, Eghbali M, Stefani E, Toro L. J Physiol (2006) 570:65-72.
18. Meredith A L, et al. J Biol Chem (2004) 279:36746-36752.
19. Pietrzykowski A Z, et al. Neuron (2008) 59:274-287.
20. Quirk J C, Reinhart P H. Neuron (2001) 32:13-23.
21. Ruttiger L, et al. Proc Natl Acad Sci USA (2004) 101: 12922-12927.
22. Sausbier M, et al. Proc Natl Acad Sci USA (2004) 101: 9474-9478.
23. Shen K Z, et al. Pflugers Arch (1994) 426:440-445.
24. Shipston M J (2001) Trends Cell Biol 11:353-358.
25. Tian L, et al. J Biol Chem (2001) 276:7717-7720.
26. Tseng-Crank J, et al. Neuron (1994) 13:1315-1330.
27. Wang S X, Ikeda M, Guggino W B J Biol Chem (2003) 278:2713-2722.
28. ie J, McCobb D P Science (1998) 280:443-446.
29. Zarei M M, Zhu N, et al. J Biol Chem (2001) 276:16232-16239.
30. Zarei M M, et al. Proc Natl Acad Sci USA (2004) 101: 10072-10077.
31. Zarei M M, et al. Neuroscience (2007) 147:80-89.

What is claimed is:

1. A peptide modulator that increases the surface expression of $Ca^{2+}$-activated potassium channels, wherein said peptide modulator consists of a C-terminal sequence selected from the group consisting of: SEQ ID NO: 9, SEQ ID NO: 12, SEQ ID NO: 13, SEQ ID NO: 14, SEQ ID NO: 15, SEQ ID NO: 16, SEQ ID NO: 17, SEQ ID NO:18 and SEQ ID NO: 19.

2. The peptide modulator of claim 1, wherein said peptide modulator is attached to the C-terminal end of Slo1 protein.

3. The peptide modulator of claim 1, wherein a myristoyl group is attached to said peptide modulator.

4. The peptide modulator of claim 1, wherein a cell penetrating peptide is attached to the peptide modulator, wherein said cell penetrating peptide is selected from the group consisting of HIV-Tat, Penetratin and a Trojan peptide.

5. A method of improving electrolyte balance across a cell membrane, comprising:
   contacting the cell with the peptide modulator of claim 1.

6. The method of claim 5, wherein said peptide modulator is attached to the C-terminal end of a Slo1 protein.

* * * * *